United States Patent
Adams et al.

(10) Patent No.: US 6,644,318 B1
(45) Date of Patent: Nov. 11, 2003

(54) INFANT EMERGENCY NECK RESTRAINT

(76) Inventors: Gail M. Adams, 6 Deerfield Dr., Warwick, RI (US) 02886; Joyce L. Andrade, 6 Deerfield Dr., Warwick, RI (US) 02886

(*) Notice: Subject to any disclaimer, the term of this patent is extended or adjusted under 35 U.S.C. 154(b) by 0 days.

(21) Appl. No.: 10/238,634

(22) Filed: Sep. 11, 2002

(51) Int. Cl.$^7$ ................................................. A61B 19/00
(52) U.S. Cl. ............................ 128/869; 128/870; 5/628
(58) Field of Search ................................ 128/845, 846, 128/869, 870, 874, 875; 5/630, 637, 638, 628, 624

(56) References Cited

U.S. PATENT DOCUMENTS

| | | | |
|---|---|---|---|
| 3,774,825 A | * 11/1973 | Schone | ........................ 224/25 |
| 3,897,777 A | 8/1975 | Morrison | |
| 4,043,325 A | 8/1977 | Ochs et al. | |
| 4,492,225 A | * 1/1985 | Picolet | ..................... 128/87 R |
| 4,665,908 A | 5/1987 | Calkin | |
| 4,735,423 A | * 4/1988 | Foss | ............................ 280/18 |
| 4,979,520 A | 12/1990 | Boone, Jr. et al. | |
| 6,276,365 B1 | * 8/2001 | Stelzenmuller | ............. 128/820 |

* cited by examiner

Primary Examiner—Michael A. Brown
(74) Attorney, Agent, or Firm—Richard C. Litman

(57) ABSTRACT

An emergency neck restraint for small children and infants. This restraint is designed to be adjustable to fit the necks of infants and toddlers. It is made from a rectangular sheet which is reinforced on its edges. Attached to the edges of this sheet are two pairs of straps. The straps from one side of the sheet connect with the straps from the other side of the sheet. Between these straps are two slits in the sheet. When the invention is used the sheet is folded. and rolled toward and up to the slits. This rolled sheet is placed behind a patient's neck and the roll is folded in a U-shaped support around the patient's neck. The ends of the roll are connected with one pair of straps. The unrolled portion of the sheet can be folded under the patient's shoulders to align the cervical spine.

4 Claims, 4 Drawing Sheets

INFANT EMERGENCY NECK RESTRAINT

BACKGROUND OF THE INVENTION

1. Field of the Invention

The present invention relates to physical restraints and braces. In particular, this invention relates to the field of cervical restraints for infants and small children.

2. Description of the Related Art

When a person suffers a traumatic neck or spinal injury it is often necessary to immobilize the person's head and neck so as to prevent further injury. Devices designed to perform this function in adults often are not suitable for use on infants and toddlers. Problems with existing restraints include: an inability to adjust to fit small children, adjustment means that are difficult to operate, devices that are not easily washable and reusable, and the fact that existing devices do not provide support sufficient to align the cervical spine and open an infants airway.

U.S. Pat. No. 4,043,325 is typical of the prior art in this area. The '325 invention teaches of a strip of resistantly-resilient material which is of a length such that the ends of the material overlap when the material is encircled around a wearer's neck. The '325 invention also has several straps which secure they collar to a support such as a spine board, but are not used to fasten the collar around the wearer's neck. The present invention is a neck restraint of a uniform width that, unlike the device of the '325 patent, has a height between the chin and the collar bone which can be adjusted according to the size of the patient. The present invention also has a means of supporting the patient's back and thereby aligning the cervical spine and opening the infant's airway, a feature which is lacking from the '325 patent. The present invention is constructed with flexible materials which facilitate the cleaning and reuse of the restraint, a feature which is also not present in the '325 patent. Finally the present invention is specifically designed to fit toddlers and infants unlike the neck support apparatus described in the '325 patent.

Other inventions which attempt to restrain the neck after an injury, such as the device described in U.S. Pat. No. 3,897,777, require that the head of a patient be sandwiched between pillow-like lobes. These types of inventions differ from the present invention in that they require that a patient be affixed to a spine board or be lying on their backs in order to function properly as a neck restraint. Also these inventions are not easily washable and reusable, do not open airways or align the cervical vertebrae, and are not adjustable to the sizes needed for small children.

There are a number of prior art inventions, such as the apparatus described in U.S. Pat. No. 4,665,908, that restrain the neck by holding the head of a patient to a spine board or other, inflexible support. The inflexible support found in these inventions makes these devices more costly, harder to clean and reuse, impossible to adjust to fit small children and require more storage space, which is an important consideration in cramped environments, such as in an ambulance.

There are a number of patents directed to pediatric immobilization devices, such as U.S. Pat. No. 4,979,520. These devices seek to miniaturize preexisting restraint devices. They do not, however, incorporate the novel features of a flexible, adjustable neck restraint, convenient storage and back support found in the present invention.

None of the above inventions and patents, taken either singularly or in combination, is seen to describe the instant invention as claimed. Thus a infant emergency neck restraint solving the aforementioned problems is desired.

SUMMARY OF THE INVENTION

The present invention is an infant emergency neck restraint which functions to restrain the motion of a small child's head and neck after the child has suffered a spinal injury, so as to prevent further injury before treatment can be applied. The invention has a flat rectangular sheet made of fabric with a front, back, top, bottom and two sides. Two straps with a slit parallel to and extending between the straps extend from opposite sides of the sheet. The straps are positioned closer to the top portion of the sheet than the bottom portion. When in use, depending on the size of the child's neck to be supported, either the top or the bottom portion of the sheet is rolled up to the nearest set of straps. The thickness of the roll also depends on the size of the child's neck to be supported. The rolled sheet is then placed behind the child's neck. The ends of the roll are then folded in on themselves, forming a U-shaped support between the infant's jaw and clavicle line, and fastened together in front of the child's throat with one pair of straps. The unrolled portion of the sheet can then be folded under the child's shoulders to provide a shoulder roll support in order to align the cervical spine and open the child's airway.

Accordingly, it is a principal object of the invention to provide emergency cervical support to small children and infants.

It is another object of the invention to provide an adjustable, flexible emergency cervical support to small children and infants.

It is a further object of the invention to provide a cervical support to infants and children that is washable and storable in a minimum of space.

It is still another object of this invention to provide support to the shoulders of infants and toddlers sufficient to align the cervical spine and open airways.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
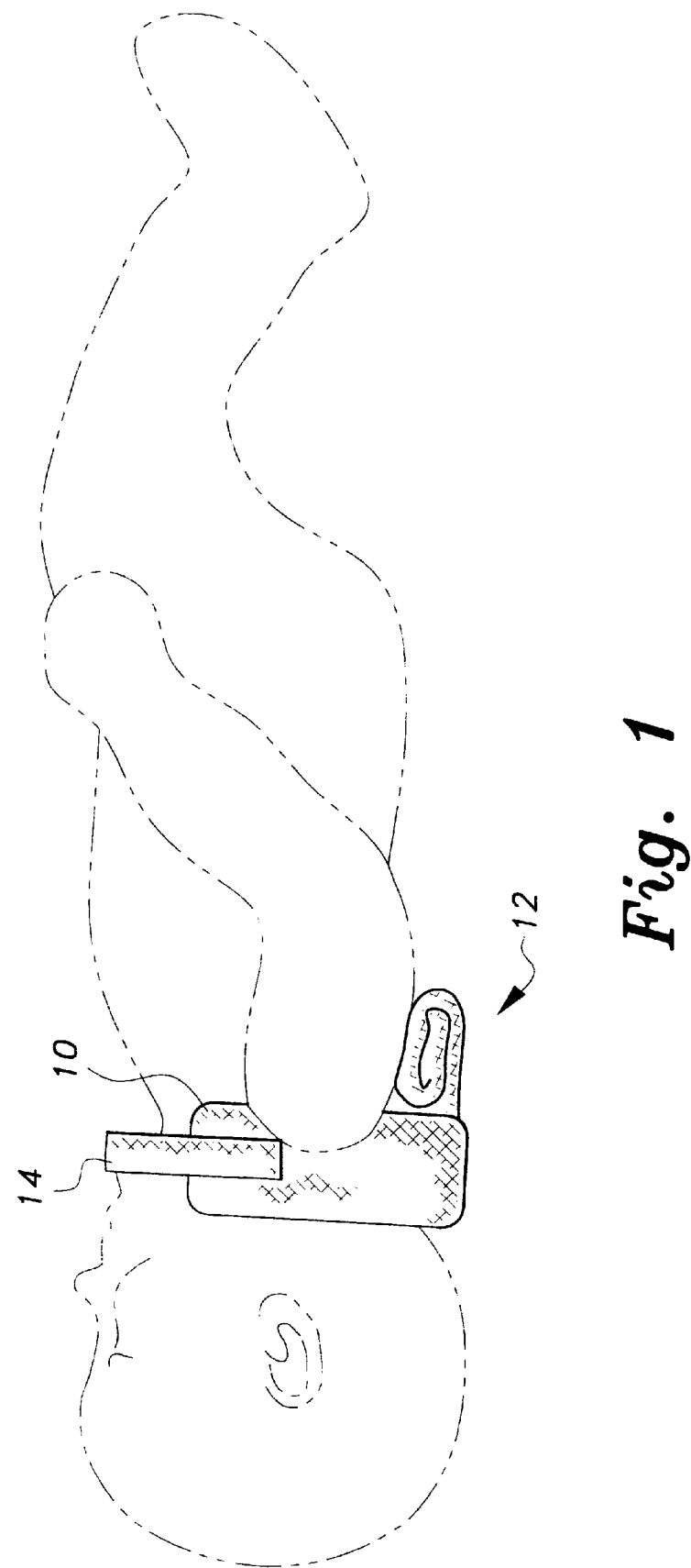
FIG. 1 is an environmental side elevation view of an infant in a neck restraint according to the present invention.
Figure 2:
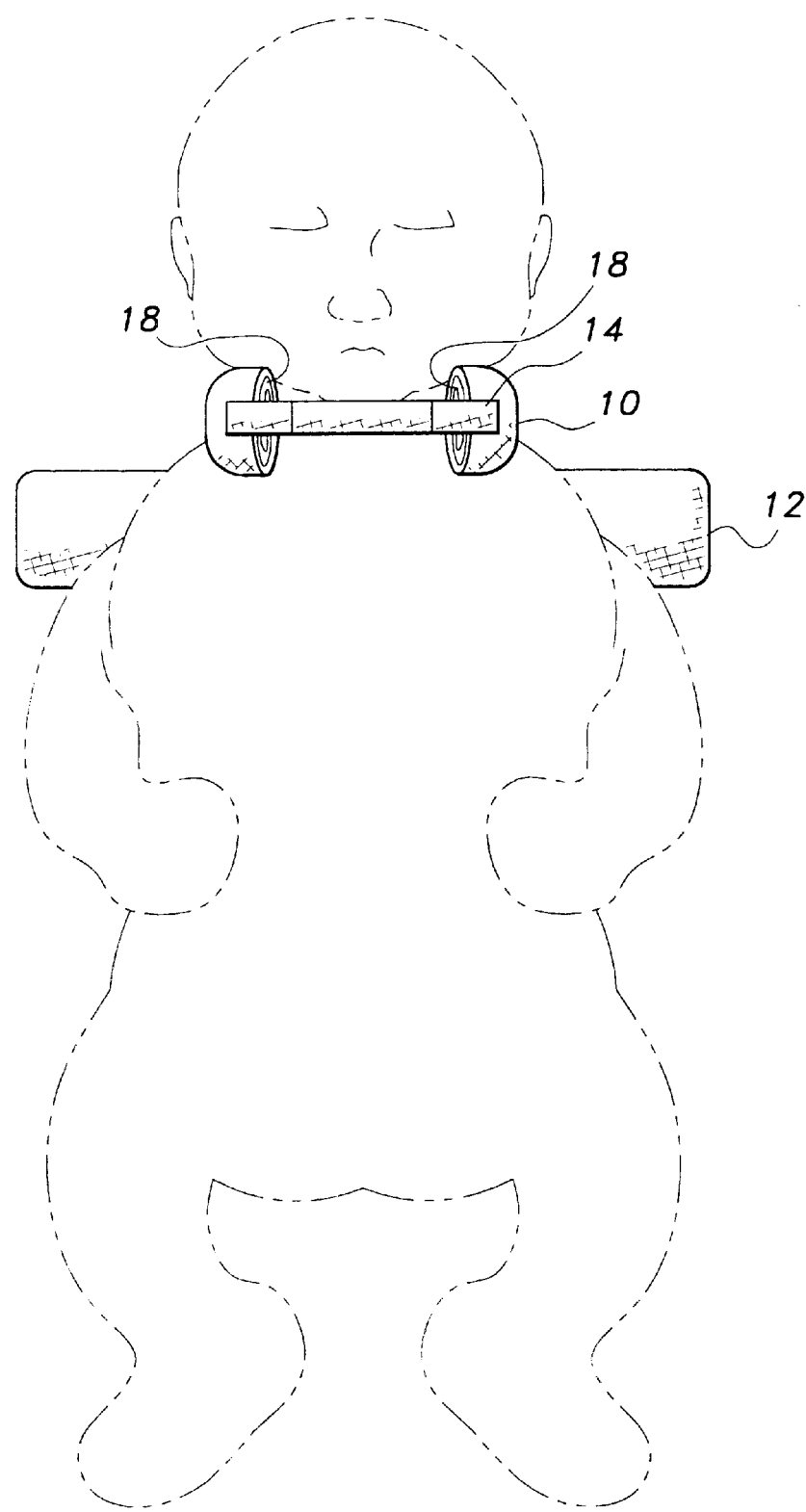
FIG. 2 is an environmental front view of an infant in a neck restraint according to the present invention.

FIGS. 1 and 2 show environmental views of the preferred embodiment of the present invention. The infant emergency neck restraint 10 is a device which may be used by emergency medical technicians or other rescue personnel, trauma centers, emergency rooms, etc. to provide a temporary neck fixation or support device for infants or toddlers in cases of suspected spinal injury, or whenever a neck support is deemed desirable. Current neck restraints or cervical collars are too large to fit a small child, are minimally adjustable, and are disposable rather than reusable. The device 10 shown in FIGS. 1 and 2 offers a solution to these problems.

Figure 3:
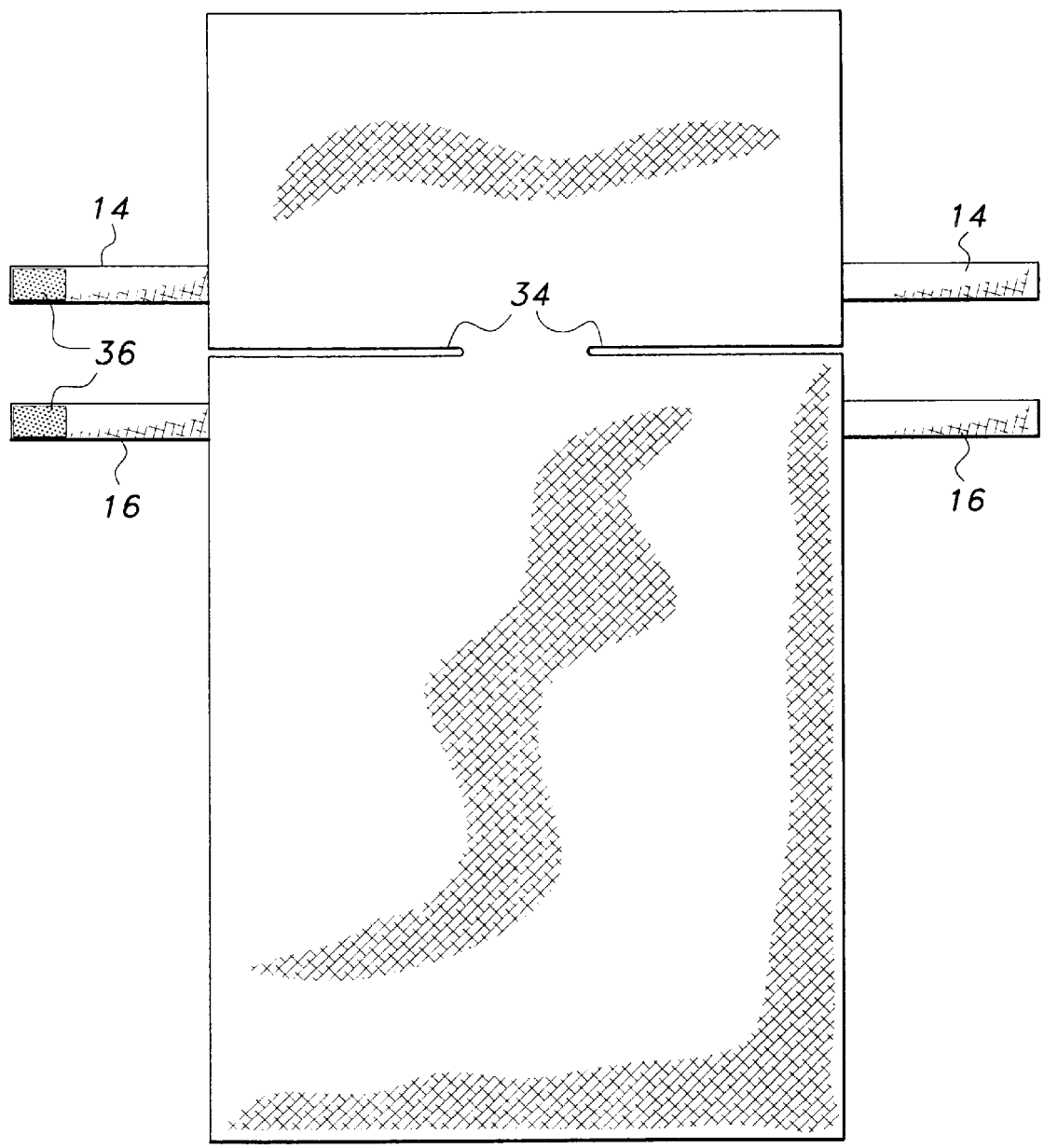
FIG. 3 is a front view of an unfolded infant. neck restraint according to the present invention.
Figure 4:
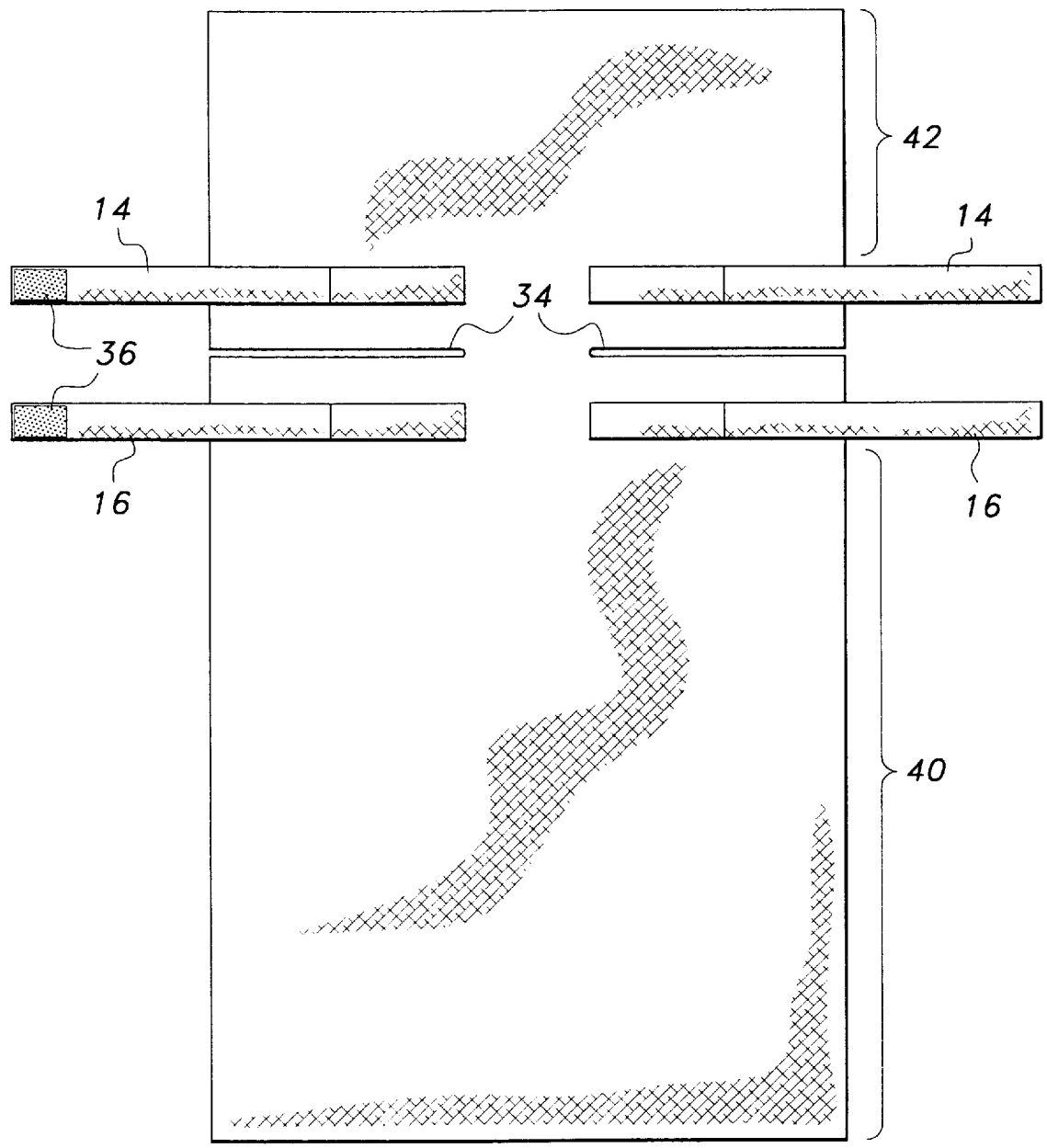
FIG. 4 is a back view of an unfolded infant neck restraint according to the present invention.

The infant emergency neck restraint 10 is a flexible rectangular sheet having a front surface (seen in FIG. 3), a back surface (seen in FIG. 4), a top, a bottom and two sides, as seen more clearly in the unfolded views shown in FIGS. 3 and 4. Preferably the sheet is reinforced around both sides, the top, and the bottom, is thirty-six inches tall and eighteen inches wide, and is made of "pack cloth" or other suitable canvas-like material. The neck restraint 10 of the present invention is therefore washable and reusable. As seen in FIG. 4, attached to the back of the sheet are two pairs of straps, including an upper pair of straps 14 and a lower pair of straps 16. The straps 14 and 16 are preferably positioned so that distance 40 between the lower straps 16 and the bottom of the sheet is longer than distance 42 between the upper pair of straps 14 and the top of the sheet. The straps 14 and 16 preferably are removably attachable to one another by means of patches or strips of hook and loop fastening material 36 which are fixed to the ends of the straps 14 and 16. Positioned between the straps 14, 16 are two slits 34 which extend parallel to the straps 14, 16 towards the midline of the sheet.

When using the invention on a larger child section 40 is rolled from the bottom up toward the pair of slits 34. If a smaller child is in need of neck support section 42 of the sheet is rolled starting at the top and proceeding down toward the slits 34. The size of the rolls depends on the distance between the child's clavicle and chin. Once the sheet has been rolled the rolled portion is placed behind the child's neck. FIG. 2 shows the two ends 18 of the rolled portion after they have been wrapped around the neck of the child and fastened together with one pair of straps. If the top portion of the sheet 42 is the rolled portion, upper straps 14 are used, as shown in FIGS. 1 and 2. If the bottom portion of the sheet 40 has been rolled, lower straps 16 are used to secure the ends of the rolled portion. Since the sheet of material is flexible, the height of the rolled portion placed around the child's neck between the chin and the clavicle can be adjusted by changing the size of the folds while rolling the sheet.

FIG. 1 shows that the remaining unrolled portion of the sheet 12 can be folded and positioned under the child's shoulders so as to align the cervical vertebra and open the airway.

It is to be understood that the present invention is not limited to the embodiments described above, but encompasses any and all embodiments within the scope of the following claims.

We claim:

1. An adjustable infant emergency neck restraint comprising:

a flexible rectangular flat sheet having a top, bottom, two opposing sides, a front surface and a back surface, said sheet having a slit extending from each of the opposing sides towards a midline of said sheet, the slits defining an upper portion and a lower portion of said sheet;

an upper pair of straps attached to the opposing sides of said sheet between the slits and the top of said sheet, and a lower pair of straps attached to the opposing sides of said sheet between the slits and the bottom of said sheet; and fastening means for removably fastening said upper pair of straps together and for fastening said lower pair of straps, together;

wherein said upper portion and said lower portion of said sheet are adapted to be folded and rolled toward the slits forming a roll having two ends; and wherein said roll is adapted to be placed behind a patient's neck, said ends being brought together to form a U-shaped support around the patient's neck with one of said upper pair and said lower pair of straps being fastened together.

2. The adjustable infant emergency neck restraint as in claim 1, wherein said fastening means comprises hook and loop fastening materials.

3. The adjustable infant emergency neck restraint as in claim 1, including reinforcing material on said top, bottom and sides of said sheet.

4. An adjustable infant emergency neck restraint as in claim 1 constructed of pack cloth.

* * * * *